United States Patent [19]

Girgis et al.

[11] Patent Number: 5,284,985
[45] Date of Patent: Feb. 8, 1994

[54] PROCESS FOR THE SELECTIVE HYDROCRACKING OF DISTILLATES TO PRODUCE NAPHTA RANGE HIGH OCTANE ISOPARAFFINS

[75] Inventors: Michael J. Girgis, Lawrenceville, N.J.; Ying-Yen P. Tsao, Lahaska, Pa.

[73] Assignee: Mobil Oil Corp., Fairfax, Va.

[21] Appl. No.: 955,774

[22] Filed: Oct. 5, 1992

[51] Int. Cl.$^5$ .............................. C07C 5/27
[52] U.S. Cl. ............................ 585/310; 585/739; 208/49; 208/111
[58] Field of Search ............ 585/739, 310; 208/49, 208/210

[56] References Cited

U.S. PATENT DOCUMENTS

| 4,518,485 | 5/1985 | LaPierre et al. | 585/739 |
| 4,554,065 | 11/1985 | Albinson et al. | 585/736 |
| 4,665,273 | 5/1987 | Johnson et al. | 208/138 |
| 4,778,944 | 10/1988 | Zarchy | 585/751 |
| 4,851,109 | 7/1989 | Chen et al. | 585/739 |
| 5,013,422 | 5/1991 | Absil et al. | 208/18 |
| 5,095,169 | 3/1992 | Skeels et al. | 585/739 |

FOREIGN PATENT DOCUMENTS 1210335 10/1970 United Kingdom .

OTHER PUBLICATIONS

Hutson, T. et al., "Phillips HF Alkylation Process for Alkylation of $C_3$, $C_4$, and $C_5$ Olefins", Handbook of Petroleum Refining Processes, 1-23 to 1-28 (1986).
Cusher, N., "UCC Total Isomerization Process (TIP)", Handbook of Petroleum Refining Proceesses, 5-3 to 5-24 (1986).
Albright, L., et al., "Alkylation of Isobutane with $C_4$ Olefins, 1. First-Step Reactions Using Sulfuric Acid Catalyst," Ind. Eng. Chem. Res., 27, 381-386 (1988).
Maxwell, I. E., "Zeolite Catalysis in Hydroprocessing Technology," Catalysis Today, 1, 385-413 (1987).

Primary Examiner—Anthony McFarlane
Attorney, Agent, or Firm—Alexander J. McKillop; Dennis P. Santini; Lori F. Cuomo

[57] ABSTRACT

The present invention provides a two-stage process for production of high-octane naphtha range isoparaffins from a feed rich in normal and/or slightly branched paraffins. In the first stage, the normal and/or slightly branched paraffins are selectively converted to multi-branched paraffins and then cracked in a second stage to yield naphtha range isoparaffins which can be blended into a high-octane gasoline pool.

17 Claims, 1 Drawing Sheet

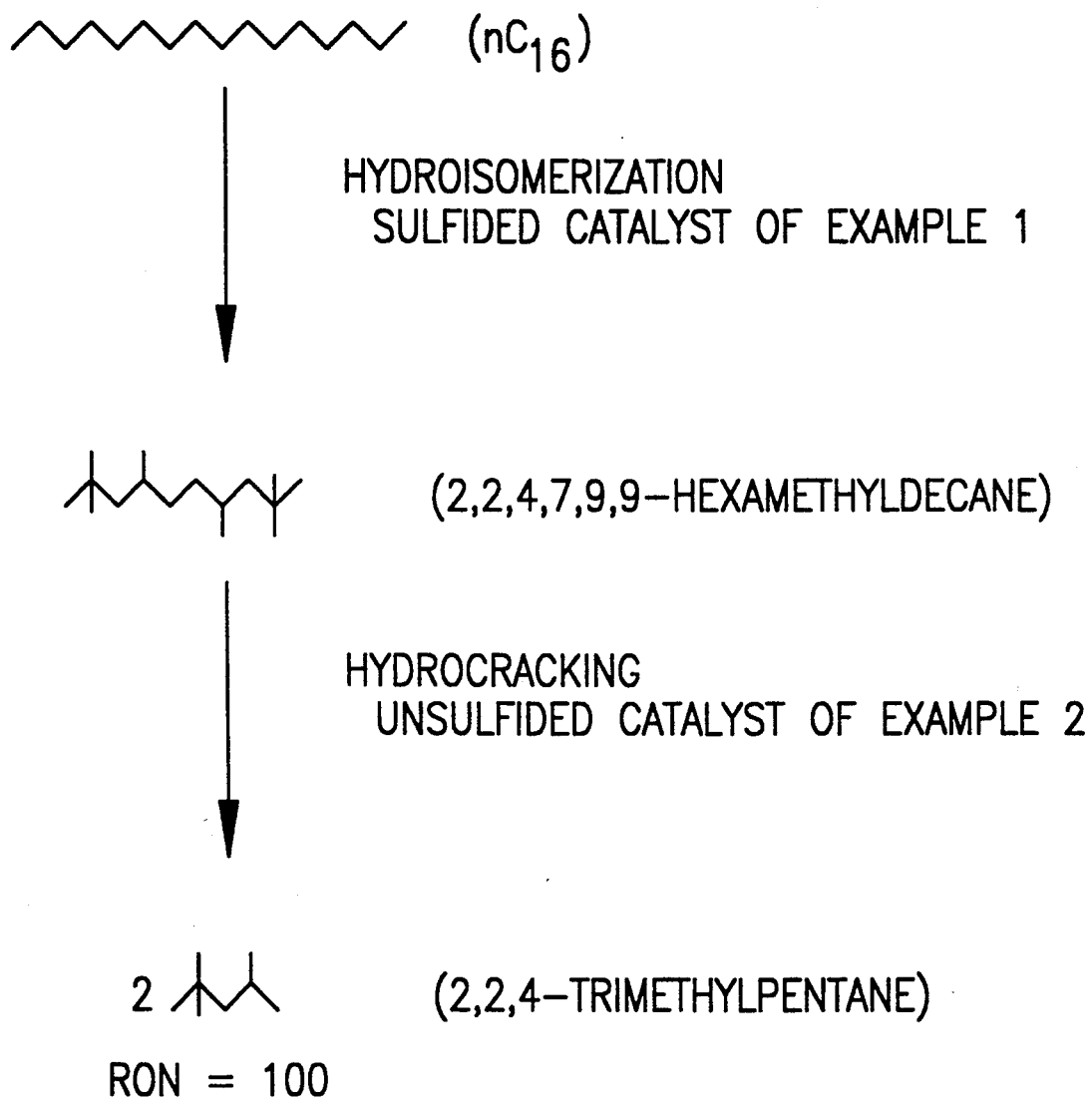

PROCESS FOR THE SELECTIVE HYDROCRACKING OF DISTILLATES TO PRODUCE NAPHTA RANGE HIGH OCTANE ISOPARAFFINS

FIELD OF THE INVENTION

This invention relates to the production of high octane isoparaffins for gasoline blending.

BACKGROUND OF THE INVENTION

Because of environmental concerns there is a great demand to develop a process for producing high octane isoparaffins for blending in the gasoline pool. Isoparaffins are conventionally produced by isomerization. In isomerization, as conventionally operated, low molecular weight $C_4$ to $C_6$ n-paraffins are converted to isoparaffins in the presence of an acidic catalyst such as aluminum chloride or an acidic zeolite, as described in G.B. Patent No. 1,210,335. Isomerization processes for pentane and hexane which operate in the presence of hydrogen have also been proposed using acidic catalysts. See Maxwell, I.E., "Zeolite Catalysis in Hydroprocessing Technology," *Catalysis Today.* 1, 385–413 (1987) and Meyers, R.A., *Handbook of Petroleum Refining Processes*, 5-3 to 5-24 (1986).

High octane isoparaffins are also produced by acid catalyzed alkylation of an isoparaffin with an olefin. Industrial alkylation processes have historically used hydrofluoric or sulfuric acid catalysts. For a general discussion of sulfuric acid alkylation, see the series of three articles by L.F. Albright et al., "Alkylation of Isobutane with $C_4$ Olefins," *Ind. Eng. Chem. Res.*, 27, 381-39, (1988). For a survey of hydrofluoric acid catalyzed alkylation, see Handbook of Petroleum Refining Processes, 23-28 (1986).

The process of the present invention avoids several disadvantages over prior art processes as the process of the present invention is not limited to $C_7$—feeds or the use of a corrosive acid catalyst.

SUMMARY OF THE INVENTION

We have now devised a two-stage process for producing high octane naphtha range isoparaffins from waxy distillates. In the first stage, a feed comprising normal and slightly branched paraffins having 2 or less alkyl substituents is hydroisomerized using a sulfided catalyst to give multi-branched paraffins. The multi-branched paraffins from the first stage are then selectively cracked in a second stage using an unsulfided catalyst composition to naphtha range multi-branched paraffins having a boiling range of about $C_5$ to about 400° F. The resulting paraffins are more branched than those obtained by dual-function hydrocracking alone, resulting in higher octane products.

Conventional dual-function hydrocracking catalysts catalyze via a different route than the process of the present invention. Paraffin conversion using conventional dual-function hydrocracking catalysts, such as NiW, Pd, or Pt as the metal component, with USY, proceeds via an acid catalyzed carbenium ion mechanism. Cracking by this mechanism occurs preferentially at the carbon bonds having at least one carbon atom with an alkyl substituent resulting in products which are less branched than the paraffin reactant. The products are generally normal and mono-branched paraffins which are low in octane number.

The unsulfided catalyst composition of the present invention cracks the unsubstituted carbon-carbon bonds preferentially as compared to conventional dual function hydrocracking catalysts which crack the carbon-carbon bonds having an alkyl substiutuent preferentially. In addition yields of low end cracking products, such as methane, ethane and propane are minimized using the unsulfided catalyst composition of this invention.

The invention therefore includes a process for producing high octane naphtha range isoparaffins from a hydrocarbon feed comprising normal and/or slightly branched paraffins having 2 or less alkyl substituents, which comprises
 (i) hydroisomerizing the feed over a sulfided catalyst composition to convert said normal and/or slightly branched paraffins to high molecular weight multi-branched paraffins;
 (ii) hydrocracking said high molecular weight multi-branched paraffins present in the effluent from the hydroisomerization step in the presence of an unsulfided catalyst composition to a product comprising high octane naphtha range isoparaffins.

BRIEF DESCRIPTION OF THE DRAWING

The Figure is a simplified illustration of the reaction pathway of the process of the present invention.

DETAILED DESCRIPTION

According to the present invention, the hydrocarbon feed rich in normal and slightly branched paraffins having 2 or less alkyl substituents is subjected to a two-stage hydroisomerization-hydrocracking process. In the first stage, the feed is subjected to a deep hydroisomerization over a sulfided low acidity dual-function catalyst to multi-branched paraffins with minimal cracking. The second stage comprises a hydrocracking step which is carried out over an unsulfided noble metal-containing zeolitic catalyst of low acidity. The catalyst for either or both of the stages may be a platinum-containing low acidity zeolite.

Feed

The feed to the process comprises n-paraffin rich feeds having a carbon number > than 12. Additionally and/or alternatively the feed comprises slightly branched paraffins having 2 or less alkyl substituents. Feedstocks which may be treated by this process include waxy feedstocks, such as high molecular weight Fischer-Tropsch waxes, hydrocracker recycle streams, gas oils, and paraffinic resids. The feed may contain up to 30 wt% and higher of normal and slightly branched paraffins having 2 or less alkyl substituents.

The process operates with a low sulfur feed having less than about 500 ppm sulfur and less than abot 50 ppm nitrogen. It is preferable that the feed to the second stage of the process have less than about 50 ppm sulfur. Hydrotreated feeds are preferred.

A preliminary hydrotreating step may be carried out using a conventional hydrotreating catalyst to remove nitrogen and sulfur and to saturate aromatics to naphthenes without substantial boiling range conversion. Hydrotreating may also be carried out between stages as required. Hydrotreating will usually improve catalyst performance and permit lower temperatures, higher space velocities, lower pressures or combinations of these conditions to be employed. Suitable hydrotreating catalysts generally comprise a metal hydrogenation component, usually a Group VIA or VIIIA metal.

First-Stage Hydroisomerization

The n-paraffin rich feed is subjected to a two-step hydroisomerization-hydrocracking process in which both the steps are normally carried out in the presence of hydrogen. This stage is carried out at a hydrogen pressure in the range of about 400 to about about 800 psig.

In the first stage the conditions ar optimized for hydroisomerization of the normal and slightly branched paraffins in the feed to high molecular weight multi-branched paraffins. The high molecular weight multi-branched paraffins generally have at least 4 alkyl substituents and preferably at least 6 alkyl substituents. For this purpose a sulfided low acidity catalyst with high isomerization selectivity is employed. Generally, the temperature will be in the range of about 300° to about 350° C. and the space velocity will be in the range of 0.1–1.0 LHSV, hr$^{-1}$.

The catalyst used in the first stage is one which has a high selectivity for the isomerization of normal and slightly branched paraffins to multi-branched paraffin products. Catalysts of this type are dual-function in nature comprising a metal component on a large-pore size, porous support of relatively low acidity. In general terms an Alpha Value below about 30 should be employed, with preferred Alpha Values below about 5.

The acidity of the catalyst may be measured by its Alpha Value. When Alpha Value is examined, it is noted that the Alpha Value is an approximate indication of the catalytic cracking activity of the catalyst compared to a standard catalyst and it gives the relative rate constant (rate of normal hexane conversion per volume of catalyst per unit time). It is based on the activity of the highly active silica-alumina cracking catalyst taken as an Alpha of 1 (Rate Constant=0.016 sec$^{-1}$). The Alpha Test is described in U.S. Pat. No. 3,354,078; in the *Journal of Catalysis*, 4, 527 (1965); 6, 278 (1966); and 61, 395 (1980), each incorporated herein by reference as to that description. The experimental conditions of the test used herein include a constant temperature of 538° C. and a variable flow rate as described in detail in the *Journal of Catalysis*, 61, 395 (1980).

The first-stage catalyst also includes a metal component in order to promote the desired hydroisomerization reactions which, proceeding through unsaturated transitional species, require mediation by a hydrogenation-dehydrogenation component. In order to maximize the isomerization activity of the catalyst, metals having a strong hydrogenation function are preferred and for this reason, platinum and the other noble metals such as palladium are given a preference. The amount of the noble metal hydrogenation component is typically in the range 0.5 to 5 weight percent of the total catalyst, usually from 0.5 to 2 weight percent. The platinum may be incorporated into the catalyst by conventional techniques including ion exchange with complex platinum cations such as platinum tetraammine or by impregnation with solutions of soluble platinum compounds, for example, with platinum tetraammine salts such as platinum tetraamminechloride. The catalyst may be subjected to a final calcination under conventional conditions in order to convert the noble metal to the oxide form and to confer the required mechanical strength on the catalyst.

The metals present in the dual function catalyst are used in their sulfided form and to this purpose presulfiding of the catalyst should be carried out prior to initiation of the hydroisomerization. Sulfiding is an established technique and it is typically carried out by contacting the catalyst with a sulfur-containing gas usually in the presence of hydrogen. The mixture of hydrogen and hydrogen sulfide, carbon disulfide or a mercaptan such as butyl mercaptan is conventional for this purpose. Presulfiding may also be carried out by contacting the catalyst with hydrogen and a sulfur-containing hydrocarbon oil such as sour kerosene or gas oil.

Zeolite Beta is the particularily preferred zeolite for use as the support material in the first stage of the process. Zeolite Beta is described in U.S. Pat. Nos. 3,308,069 and Re No. 28,341, incorporated herein by reference.

Other useful zeolites include steamed 12-membered ring materials, including USY and multi-channel SAPO-type molecular sieves, such as SAPO-37. Low sodium Ultra Stable Y molecular sieve (USY) is described in U.S. Pat. Nos. 3,293,192 and 3,449,070, incorporated herein by reference. SAPO-37 is described in U.S. Pat. No. 4,898,792, incorporated herein by reference.

The desired low acidity zeolites may be prepared by direct synthesis or converted into the desired low acidity form by various techniques, such as steaming, cation exchange, calcination, and acid treatment.

Preferably, the zeolite is composited with a binder. The preferred binder is silica but other silica-containing binders may also be used, for example, silica-alumina, silica-boria, silica-magnesia, silica-zirconia, silica-thoria, silica-berylia, silica-titania a well as ternary compositions such as silica-alumina-boria, silica-alumina-thoria, silica-alumina-zirconia, silica-alumina-magnesia, or silica-magnesia-zirconia. The ratio of binder to zeolite will typically vary from about 9:1 to about 1:9, more commonly from about 3:1 to about 1:3 (by weight).

The preferred sulfided catalyst useful in the first-stage hydroisomerization is a steamed Pt/boron-containing zeolite Beta.

Second-Stage Hydrocracking

The objective in the second stage of the process is to effect a selective hydrocracking of the high molecular weight multi-branched paraffins to naphtha range iso-paraffins.

The second stage operates at a pressure in the range of about 800 to about 2000 psig. Generally, the temperature will be in the range of about 280° to about 330° C. and the space velocity will be in the range of 0.4–2.0 LHSV, hr$^{-1}$.

The catalyst used in the second stage is one which has a high selectivity for cracking the high molecular weight multi-branched paraffins at the bonds connecting unsubstituted carbon atoms. It is the cracking at these bonds that produces highly branched, higher octane products as opposed to cracking at the branched bonds, as with conventional dual function hydrocracking catalysts.

Catalysts with this high selectivity for cracking the bonds connecting unsubstituted carbon atoms are unsulfided and possess a very low zeolite acidity. In general terms an Alpha Value below about 5 should be employed, with preferred values below about 3.

The noble metals useful in the second-stage hydrocracking catalyst include platinum, palladium, and other Group VIIIA metals such as iridium and rhodium, with platinum preferred.

The noble metal may be incorporated into the catalyst by any suitable method such as impregnation or exchange onto the zeolite. The noble metal may be incorporated in the form of a cationic, anionic or neutral complex such as $Pt(NH_3)_4^{2+}$ and cationic complexes of this type will be found convenient for exchanging metals onto the zeolite. The amount of noble metal is suitably from about 0.01 to about 10 percent by weight, normally from about 0.1 to about 2.0 percent by weight. In a preferred method of synthesizing Pt/boron-containing zeolite Beta the platinum compound is tetraamineplatinum hydroxide. The noble metal is preferably introduced into the catalyst composition with a pH neutral solution.

A high level of noble metal dispersion is preferred. For example, platinum dispersion is measured by the hydrogen chemisorption technique and is expressed in terms of H/Pt ratio. The higher the H/Pt ratio, the higher the platinum dispersion. Preferably the resulting zeolite should have an H/Pt ratio greater than about 0.8.

Zeolite Beta is the particularily preferred zeolite for use in the second stage of the process. Zeolite Beta is described in U.S. Pat. Nos. 3,308,069 and Re No. 28,341, incorporated herein by reference.

Other useful zeolites include steamed 12-membered ring materials, including USY and multi-channel SAPO type molecular sieves. Low sodium Ultra Stable Y molecular sieve (USY) is described in U.S. Pat. Nos. 3,293,192 and 3,449,070. incorporated herein by reference. SAPO-37 is decribed in U.S. Pat. No. 4,898,722, incorporated herein by reference.

The desired low acidity zeolites may be prepared by direct synthesis or converted into the desired low acidity form by various techniques, such as steaming, cation exchange, calcination, and acid treatment.

Preferably, the zeolite is composited with a binder. The preferred binder is silica but other silica-containing binders may also be used, for example, silica-alumina, silica-boria, silica-magnesia, silica-zirconia, silica-thoria, silica-berylia, silica-titania as well as ternary compositions such as silica-alumina-boria, silica-alumina-thoria, silica-alumina-zirconia, silica-alumina-magnesia or silica-magnesia-zirconia. The ratio of binder to zeolite will typically vary from about 9:1 to about 1:9, more commonly from about 3:1 to about 1:3 (by weight).

The preferred unsulfided catalyst useful in the second-stage hydrocracking is a steamed Pt/boron-containing zeolite Beta.

The following examples illustrate the process of the present invention.

EXAMPLE 1

The first-stage hydroisomerization catalyst is a sulfided boron-containing zeolite Beta. An ammonium form of zeolite Beta, prepared in accordance with U.S. Pat. No. 3,308,069 and Re No. 28,341 and containing 2.0% boron is first subjected to steam treatment at 552° C. for 16 hours. The resultant catalyst is exchanged with an aqueous solution of tetraamine platinum hydroxide for 16 hours. The catalyst is then dry air calcined at 350° C. for 4 hours. The resulting catalyst had a Pt loading of 0.70% and a B content of 0.11%, based on elemental analysis. Pt dispersion expressed as H/Pt, is 1.29, indicating well dispersed Pt particles.

The catalyst is then subjected to a 4 hour 350° C. sulfiding treatment using 2% $H_2S/H_2$ prior to introduction of the feed.

EXAMPLE 2

The second-stage hydrocracking catalyst is an unsufided boron-containing zeolite Beta. An ammonium form of zeolite Beta, prepared in accordance with U.S. Pat. No. 3,308,069 and Re No. 28,341 and containing 2.0% boron is first subjected to steam treatment at 552° C. for 16 hours. The resultant catalyst is exchanged with an aqueous solution of tetraamine platinum hydroxide for 16 hours. The catalyst is then dry air calcined at 350° C. for 4 hours. The resulting catalyst has a Pt loading of 0.70% and a B content of 0.11%, based on elemental analysis. Pt dispersion expressed as H/Pt, is 1.29, indicating well dispersed Pt particles.

EXAMPLE 3

A feed comprising $nC_{16}$ is converted using the two-stage process of the present invention. As shown in the Figure, $nC_{16}$ is first selectively hydroisomerized over the catalyst of Example 1 resulting in highly branched $C_{16}$ isomers, such as 2,2,4,7,9,9-hexamethyldecane. In the second step, the hydroisomerization product is hydrocracked preferentially at unsubstituted carbon-carbon atoms over the catalyst of Example 2 with minimal end cracking, yielding a higher octane product. For example, 2,2,4,7,9,9-hexamethyldecane is converted to 2,2,4-trimethylpentane having an RON of 100.

Changes and modifications in the specifically described embodiments can be carried out without departing from the scope of the invention which is intended to be limited only by the scope of the appended claims.

What is claimed is:

1. A process for producing high octane naphtha range isoparaffins from a hydrocarbon feed comprising normal and/or slightly branched paraffins having 2 or less alkyl substituents, which comprises
   (i) hydroisomerizing the feed over a sulfided catalyst composition to convert said normal and/or slightly branched paraffins to high molecular weight multi-branched paraffins;
   (ii) hydrocracking said high molecular weight multi-branched paraffins present in the effluent from the hydroisomerization step in the presence of an unsulfided catalyst composition to a product comprising high octane naphtha range isoparaffins.

2. The process of claim 1 wherein said unsulfided catalyst composition comprises a noble metal and a low acidity crystalline zeolite having an Alpha Value of 5 or less.

3. The process of claim 2 wherein said unsulfided catalyst composition comprises platinum.

4. The process of claim 1 wherein said unsulfided catalyst composition comprises platinum and a boron-containing zeolite having the structure of zeolite Beta.

5. The process of claim 4 wherein said unsulfided catalyst composition is steamed.

6. The process of claim 1 wherein said sulfided catalyst composition comprises a noble metal and a low acidity crystalline zeolite having an Alpha Value of 30 or less.

7. The process of claim 6 wherein said sulfided catalyst composition comprises platinum.

8. The process of claim 1 wherein said sulfided catalyst composition comprises platinum and a boron-containing zeolite having the structure of zeolite Beta.

9. The process of claim 8 wherein said sulfided catalyst composition is steamed.

10. The process of claim 1 in which hydroisomerization is carried out at a temperature in the range of 300° to about 350° C., an $H_2$ pressure in the range of about 400 to about 800 psig and a space velocity in the range of about 0.1 to about 1.0 LHSV $hr^{-1}$.

11. The process of claim 1 wherein said hydrocracking is carried out at a temperature of about 280° to about 330° C., a pressure in the range of about 800 psig to about 2000 psig and a space velocity in the range of about 0.4 to about 2.0 LHSV $hr^{-1}$.

12. The process of claim 1 wherein said feed comprises $C_{12}+$ hydrocarbons.

13. The process of claim 1 wherein said high molecular weight multi-branched paraffins have at least 4 alkyl substituents.

14. The process of claim 1 wherein said sulfide catalyst composition and said unsulfided catalyst composition comprise platinum and a steamed boron-containing zeolite Beta.

15. A process for producing high octane naphtha range isoparaffins from a hydrocarbon feed comprising normal and/or slightly branched paraffins having 2 or less alkyl substituents, which comprises
  (i) hydroisomerizing the feed over a sulfided catalyst composition to convert said normal and/or slightly branched paraffins to high molecular weight multi-branched paraffins;
  (ii) hydrocracking said high molecular weight multi-branched paraffins present in the effluent from the hydroisomerization step in the presence of an unsulfided catalyst composition, wherein said unsulfided catalyst composition comprises a noble metal and a low acidity crystalline zeolite having an Alpha Value of 5 or less, to a product comprising high octane naphtha range isoparaffins.

16. A process for producing high octane naphtha range isoparaffins from a hydrocarbon feed comprising normal and/or slightly branched paraffins having 2 or less alkyl substituents, which comprises
  (i) hydroisomerizing the feed over a sulfided catalyst composition, wherein said sulfided catalyst composition is prepared by presulfiding prior to the initiation of hydroisomerization, to convert said normal and/or slightly branched paraffins to high molecular weight multi-branched paraffins;
  (ii) hydrocracking said high molecular weight multi-branched paraffins present in the effluent from the hydroisomerization step in the presence of an unsulfided catalyst composition to a produce comprising high octane naphtha range isoparaffins.

17. The process of claim 16 wherein said sulfided catalyst composition comprises platinum and a boron-containing zeolite having the structure of zeolite Beta.

* * * * *

UNITED STATES PATENT AND TRADEMARK OFFICE
CERTIFICATE OF CORRECTION

PATENT NO. : 5,284,985
DATED : February 8, 1994
INVENTOR(S) : M. J. Girgis and Y. P. Tsao It is certified that error appears in the above-indentified patent and that said Letters Patent is hereby corrected as shown below:

In Col. 8, line 24, "produce" should be --product--

Signed and Sealed this

Sixteenth Day of August, 1994

Attest:

BRUCE LEHMAN

Attesting Officer      Commissioner of Patents and Trademarks